United States Patent
Mortara et al.

(10) Patent No.: US 11,576,617 B2
(45) Date of Patent: Feb. 14, 2023

(54) DETECTING ARTIFACTS IN A SIGNAL

(71) Applicant: Welch Allyn, Inc.

(72) Inventors: David W Mortara, Milwaukee, WI (US); Patrick J. Noffke, Hartland, WI (US); Reyhaneh Sepehr, Fox Point, WI (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 242 days.

(21) Appl. No.: 17/006,461

(22) Filed: Aug. 28, 2020

(65) Prior Publication Data
US 2021/0059610 A1    Mar. 4, 2021

Related U.S. Application Data

(60) Provisional application No. 62/894,238, filed on Aug. 30, 2019.

(51) Int. Cl.
*A61B 5/00* (2006.01)
*A61B 5/25* (2021.01)
(Continued)

(52) U.S. Cl.
CPC .............. *A61B 5/7203* (2013.01); *A61B 5/25* (2021.01); *A61B 5/316* (2021.01); *A61B 5/339* (2021.01);
(Continued)

(58) Field of Classification Search
CPC ....... A61B 5/7203; A61B 5/339; A61B 5/366; A61B 5/316; A61B 5/25; A61B 2562/227
See application file for complete search history.

(56) References Cited

U.S. PATENT DOCUMENTS

| | | | |
|---|---|---|---|
| 4,263,919 A | * | 4/1981 | Levin .................... A61B 5/7214 600/521 |
| 2005/0043640 A1 | * | 2/2005 | Chang .................. A61B 5/0006 600/509 |

(Continued)

OTHER PUBLICATIONS

Drew et al., "Insights into the Problem of Alarm Fatigue with Physiologic Monitor Devices: A Comprehensive Obervational Study of Consecutive Intensive Care Unit Patients", PLOS ONE, Oct. 2014, vol. 9, Issue 10, pp. 1-pp. 23.

*Primary Examiner* — Catherine M Voorhees
*Assistant Examiner* — Roland Dinga
(74) *Attorney, Agent, or Firm* — Lee & Hayes, P.C.

(57) ABSTRACT

This disclosure is directed towards detecting artifacts in an ECG signal. An ECG system may include multiple sensors which can sense an ECG signal when attached to a patient. Bipolar leads connect the sensors, and provide the ECG signal from the sensors to a computing device. The computing device receives respective signals from the bipolar leads, where the respective signals are indicative of the ECG signal. The computing device identifies, based on the respective signals, a potential artifact corresponding to a subset of the plurality of bipolar leads. The computing device determines that each lead of the subset of the plurality of bipolar leads is connected to a common sensor. The computing device may use signals originating from a remainder of the bipolar leads (e.g., the bipolar leads that are not connected to the sensor(s) where the artifact is detected) to detect a condition of the patient.

20 Claims, 7 Drawing Sheets

(51) Int. Cl.
   *A61B 5/316*   (2021.01)
   *A61B 5/339*   (2021.01)
   *A61B 5/366*   (2021.01)

(52) U.S. Cl.
   CPC ........ *A61B 5/366* (2021.01); *A61B 2562/227* (2013.01)

(56) References Cited

U.S. PATENT DOCUMENTS

| | | | | |
|---|---|---|---|---|
| 2006/0247501 A1* | 11/2006 | Ali | ................... | A61B 5/02 600/300 |
| 2007/0129639 A1* | 6/2007 | Zhang | ................... | A61B 5/726 600/509 |
| 2007/0135727 A1* | 6/2007 | Virtanen | ................ | A61B 5/369 600/544 |

* cited by examiner

DETECTING ARTIFACTS IN A SIGNAL

CROSS REFERENCE TO RELATED APPLICATIONS

This application claims priority to U.S. Patent Application No. 62/894,238, filed Aug. 30, 2019, titled "DETECTING ARTIFACTS IN A SIGNAL," the entire contents of which are incorporated herein by reference.

TECHNICAL FIELD

This application is directed to medical equipment, and in particular, to an electrocardiograph (ECG) system configured to record the electrical activity of the heart.

BACKGROUND

ECG systems typically record electrical activity of the heart using sensors, such as electrode sensors, placed in a configuration across a patient's body. Electrode sensors of ECG systems may be connected by bipolar leads, which transfer the electrical signals sensed by the electrode sensors to a device which may aggregate the electrical signals into a single ECG signal and output ECG signal on a display device. For ECG systems where a patient may be in motion (e.g., intentionally or unintentionally), an ECG signal may contain information indicative of cardiac electrical activity, as well as other non-heart related "artifacts." Such artifacts may result from a variety of internal and external causes including, for example, the electrical activity of muscle tissue, electrical interference from external sources, poor electrode sensor contact, etc. Differentiating between cardiac electrical activity of the heart and artifacts detected by the ECG system may, at times, present challenges.

The various example embodiments of the present disclosure are directed toward overcoming one or more of the deficiencies associated with known ECG systems.

SUMMARY

Broadly, the systems and methods disclosed and contemplated herein are directed toward detecting artifacts in an ECG signal. In some examples, an ECG system may include a plurality of sensors which can sense an ECG signal when attached to a patient. Bipolar leads may be connected to the plurality of sensors, and may provide the ECG signal from the sensors to a computing device. The computing device may receive respective signals from the bipolar leads, where the respective signals are indicative of the ECG signal. The computing device may identify, based on the respective signals, a potential artifact corresponding to a subset of the plurality of bipolar leads. In examples, the computing device may determine that each lead of the subset of the plurality of bipolar leads is connected to at least one common sensor. Based on determining that each lead is connected to at least one common sensor, the computing device may identify signals originating from the remainder of the bipolar leads (e.g., the bipolar leads that are not connected to the sensor(s) where the artifact is detected), and use the signals originating from the remainder of the bipolar leads to detect different conditions of the patient, such as a QRS complex.

DETAILED DESCRIPTION

Figure 1:
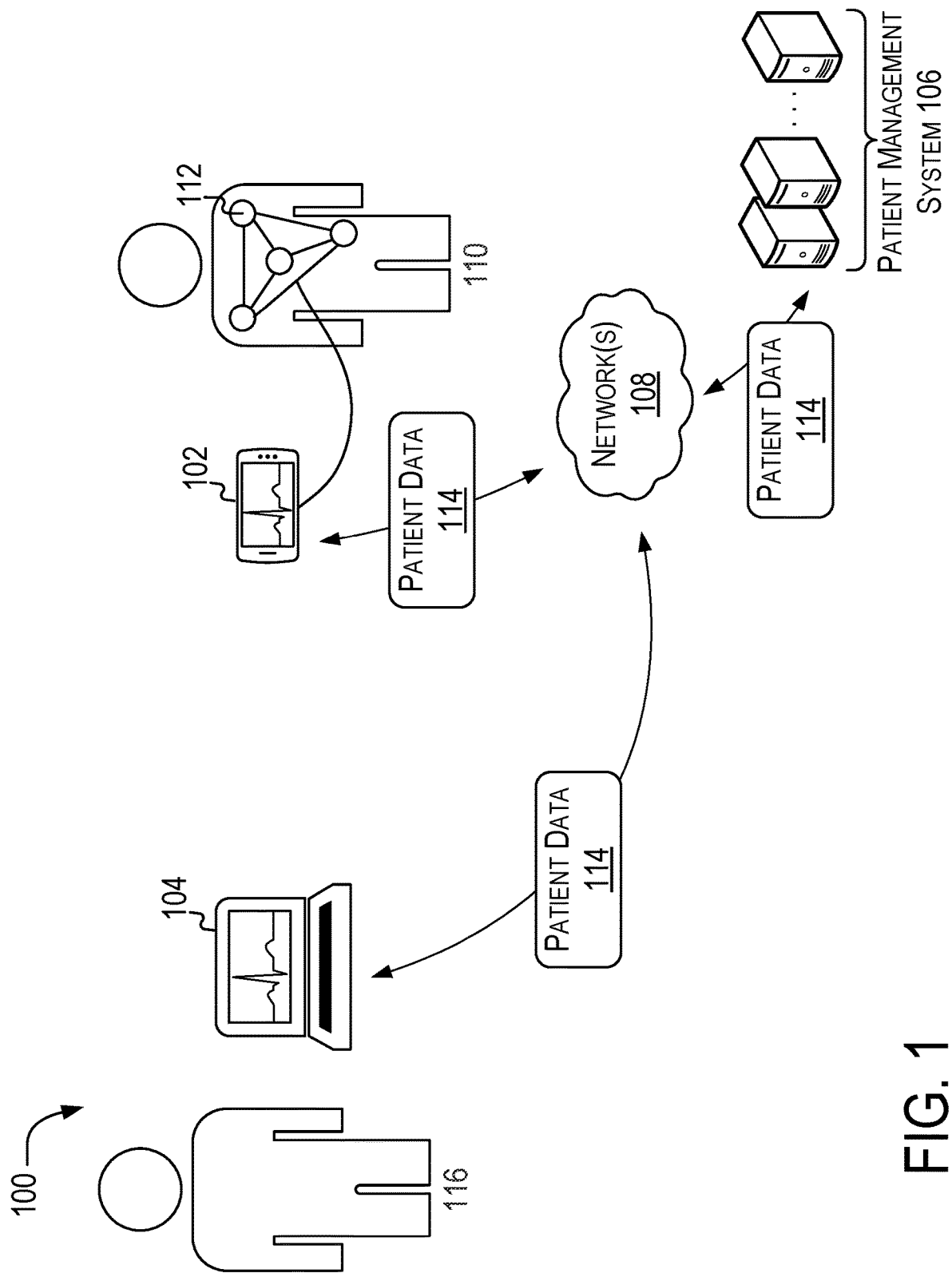
FIG. 1 shows a schematic block diagram of an example ECG system environment.

Various embodiments of the present disclosure will be described in detail with reference to the drawings, wherein like reference numerals represent like parts and assemblies throughout the several views. Additionally, any examples set forth in this specification are not intended to be limiting and merely set forth some of the many possible embodiments.

FIG. 1 shows a schematic block diagram of an example ECG system environment 100. The example ECG system environment 100 includes at least one cardiograph device 102, a display device 104, and a patient management system 106. The cardiograph device 102, the display device 104, and the patient management system 106 are in communication via a network 108. The depicted ECG system environment also includes a patient 110, and as shown in FIG. 1, the patient 110 has one or more ECG sensors 112 attached to different portions of the body of the patient 110. The ECG sensors 112 may output electrical signals of the patient 110 to the cardiograph device 102. In turn, the cardiograph device 102 may analyze and/or aggregate the electrical signals received from the ECG sensors 112, and display and/or record an ECG signal associated with the patient 110.

The cardiograph device 102 may output patient data 114 to the patient management system 106 and/or the display device 104 via the network 108. The patient data 114 may include a record of an ECG signal of the patient 110 generated by the cardiograph device 102, and/or other information associated with the patient 110 (e.g., name, date of test, pulse rate, blood pressure, etc.). In some examples, the cardiograph device 102 may be configured to detect a QRS complex associated with the ECG signal, where the QRS complex corresponds to depolarization of the right and left ventricles of the heart of the patient 110, along with contraction of the ventricular muscles of the heart. Furthermore, in some examples, the cardiograph device 102 may be configured to detect artifacts in the ECG signal, which may be associated with electrical signals generated by muscle tissue or other electrical signal sources, and remove portions of the ECG signal that are associated with such artifacts. The cardiograph device 102 may also be configured to detect artifacts caused by an arrhythmia or other heart defect, and differentiate between heart defect artifacts and other types of artifacts by determining which sensors detect an artifact according to the described techniques. The cardiograph device 102 may then selectively aggregate electrical signals from the one or more ECG sensors 112 into the ECG signal based on a determination of whether an artifact is the result of a heart defect or some other electrical signal. The selective aggregation by the cardiograph device 102 may take place before the patient data 114 is output to the display device 104 and/or the patient management system 106, thus preventing false-positive identifications of heart-defect-related artifacts.

In some examples, the patient data 114 is output to the display device 104, which may be viewed by a clinician 116 such as a doctor, nurse, technician, and the like. The clinician 116 may view an ECG signal received at the display device 104 as part of the patient data 114, such as to determine a heart rate of the patient 110, heart defects of the patient 110, and so forth. In some cases, the display device 104 may be configured to detect an artifact from electrical signals generated by the ECG sensors 112 and received by the display device 104 from the cardiograph device 102, e.g., in lieu of the cardiograph device 102 performing such an analysis.

The patient data 114 may, in addition or alternatively, be output to the patient management system 106. The patient management system 106 may store the patient data 114, and/or detect the presence of artifacts from an ECG signal included in the patient data 114 as output by the cardiograph device 102. For instance, the patient management system 106 may detect artifacts by comparing the patient data 114 to other patients having a similar demographic (e.g., children, adults, etc.). In some cases, the patient management system 106 may output results based on a detection of an artifact, or the absence of an artifact, to one or more of the cardiograph device 102 and/or the display device 104.

The cardiograph device 102 and/or the display device 104 may include a processor, microprocessor, and/or other computing device components, shown and described below. For instance, the cardiograph device 102 and/or the display device 104 may be configured as mobile phones, tablet computers, laptop computers, etc., to deliver or communicate the patient data 114 amongst one another and to other devices.

The patient management system 106 may be comprised of one or more server computing devices, which may communicate with the cardiograph device 102 and/or the display device 104 to respond to queries, receive data, and so forth. Communication from cardiograph device 102 and/or the display device 104 occurs via network 108, where the communication can include requests for corresponding ECG signal data. A server of the patient management system 106 can act on these requests from the cardiograph device 102 and/or the display device 104, determine one or more responses to those queries, and respond back to the cardiograph device 102 and/or the display device 104. A server of the patient management system 106 may also include one or more processors, microprocessors, or other computing devices similar to the cardiograph device 102 and/or the display device 104.

The patient management system 106 may include one or more database systems accessible by a server storing different types of information. For instance, a database system can store correlations and algorithms used to determine artifacts of ECG signals. A database system can also include clinical data. A database may reside on a server of the patient management system 106 or on separate computing device(s) accessible by the patient management system 106.

The techniques described herein may be performed by any of the cardiograph device 102, the display device 104, the patient management system 106, and/or other devices or components not explicitly shown or described. For example, other devices that are contemplated that may be used to implement the described techniques include (but are not limited to) bedside monitors, Holter recorders, stress test systems, and so forth.

Network 108 is typically any type of wireless network or other communication network known in the art. Examples of network 108 include the Internet, an intranet, a wide area network (WAN), a local area network (LAN), and a virtual private network (VPN), cellular network connections and connections made using protocols such as 802.11a, b, g, n and/or ac. Example configurations of the cardiograph device 102, and methods for its use, are shown and described with reference to at least FIGS. 2-6 below.

Figure 2:
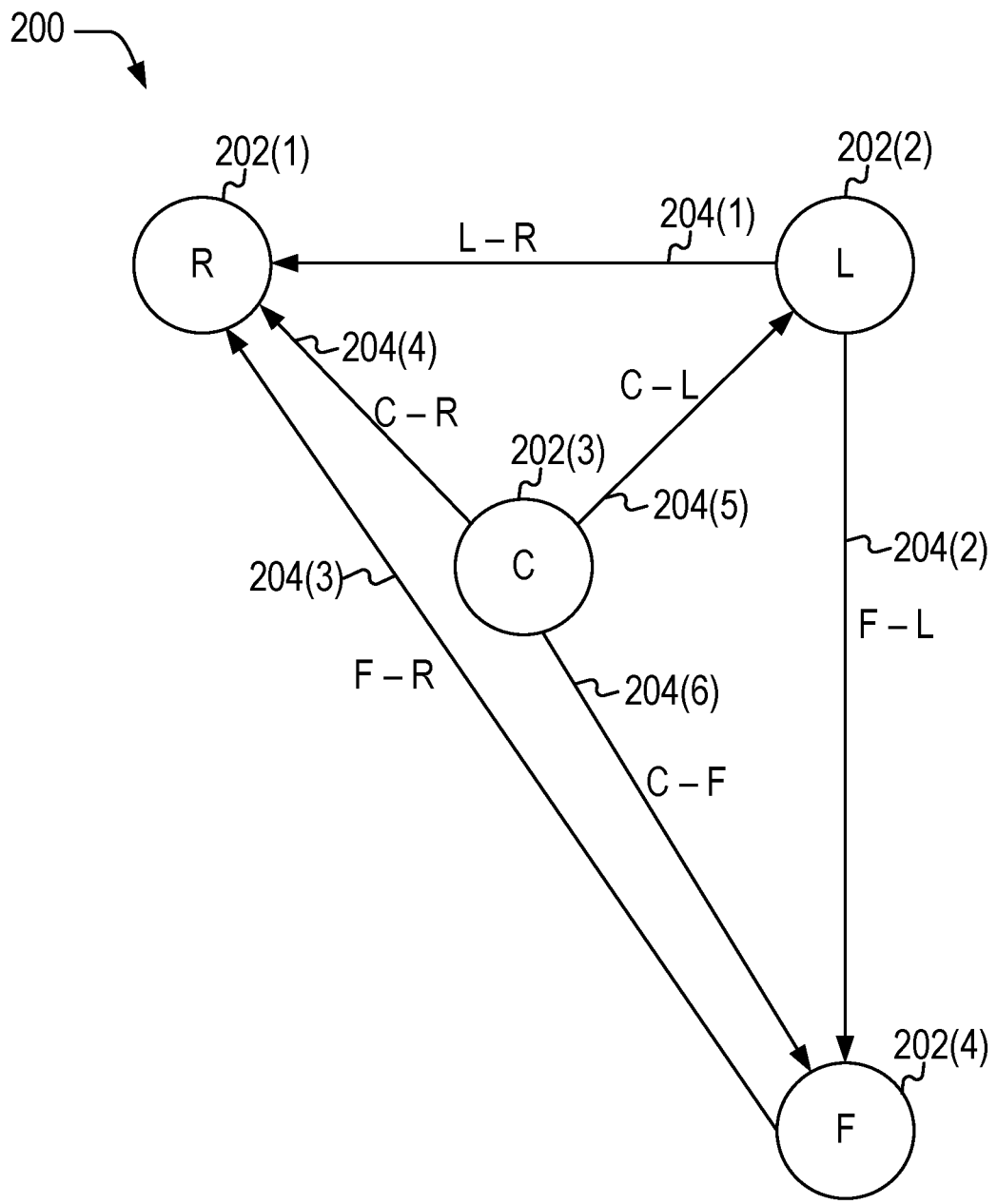
FIG. 2 shows a diagram of components of an ECG system used in the ECG system environment of FIG. 1.

FIG. 2 shows a diagram of components of an ECG system 200 used in the ECG system environment of FIG. 1. For instance, the ECG system 200 includes a sensor 202(1), a sensor 202(2), a sensor 202(3), and a sensor 202(4) (collectively, "sensors 202"), which may correspond to the ECG sensors 112 of FIG. 1. The sensors 202 may be electrode sensors configured to generate an electric field to detect the disturbance in the field caused by objects or a phenomenon. The sensors 202 may be affixed to a patient in a variety of configurations to collect electrical signals, which may be transmitted by a system of bipolar leads to a cardiograph device to generate an ECG signal for the patient. One example configuration is a 12-lead configuration using the Mason-Likar exercise lead system. In the Mason-Likar exercise lead system, two sensors (in this case, electrodes) are placed on the torso of the patient with one electrode near each shoulder, two electrodes are placed on the lower abdomen of the patient with one electrode near each leg, and six precordial electrodes are placed on the chest of the patient in a particular configuration. Other configurations are also considered, such as a conventional lead placement, in which electrodes are placed on the arms and legs rather than near the shoulders and on the lower abdomen.

In some examples, the sensor 202(1) corresponds to a sensor placed at or near a right arm of a patient (denoted by "R"), the sensor 202(2) corresponds to a sensor placed at or near a left arm of the patient (denoted by "L"), the sensor 202(3) corresponds to one or more sensors placed on the chest of the patient (e.g., precordial electrodes, collectively, and denoted by "C"), and the sensor 202(4) corresponds to a sensor placed at or near the left leg of the patient (denoted by "F"). Additional sensors may be included but are not pictured in the ECG system 200, such as a sensor placed at or near a right leg of the patient (e.g., to be used as a reference).

The sensors 202 may be connected, one to another, by a system of bipolar leads. Individual ones of the bipolar leads may be used to measure an electrical potential difference between two of the sensors 202 to which a bipolar lead is attached. The ECG system 200 includes a bipolar lead 204(1), a bipolar lead 204(2), a bipolar lead 204(3), a bipolar lead 204(4), a bipolar lead 204(5), and a bipolar lead 204(6) (collectively bipolar leads 204). In this example, the bipolar lead 204(1) is connected to the sensor 202(1) and the sensor 202(2), the bipolar lead 204(2) is connected to the sensor 202(2) and the sensor 202(4), the bipolar lead 204(3) is connected to the sensor 202(4) and the sensor 202(1), the bipolar lead 204(4) is connected to the sensor 202(3) and the sensor 202(1), the bipolar lead 204(5) is connected to the sensor 202(3) and the sensor 202(2), and the bipolar lead 204(6) is connected to the sensor 202(3) and the sensor 202(4). As noted above, additional sensors may be present that are not pictured in the ECG system 200, and thus additional bipolar leads that are not pictured may be present as well that connect one sensor to another (both for pictured and not pictured sensors).

Conventional ECG devices allow analysis on one or more of the bipolar leads 204. In some examples, a conventional ECG system may allow a user (e.g., the clinician 116 of FIG. 1) of which leads to use for analysis of electrical signals detected by the sensors 202. In these examples, an artifact present on a single electrode sensor may influence the analysis of all of the bipolar leads that have been selected. Therefore, the described techniques utilize the redundancy of the available electrical signals, along with an assumption that artifacts that are not related to a cardiac electrical activity (e.g., defects associated with electrical activity of muscle tissue) typically occur in a small number (e.g., one or two) of electrodes, to dynamically select bipolar leads for analysis. Accordingly, the described techniques provide rapid and accurate detection of artifacts, along with rejection of artifacts associated with electrical activity of muscle tissue, thus reducing false positive QRS detections, false positive arrhythmia detections, and the like, and improving patient outcomes.

For instance, the techniques described herein may detect an artifact on all bipolar leads that share a common electrode sensor. When this occurs, the electrode where the artifact was generated may be temporarily excluded from analysis and generation of the overall ECG signal. With the four sensors 202 pictured in the ECG system 200, each of the sensors 202 is present in three of the bipolar leads 204. Thus, if an artifact occurs in one of the sensors 202 (e.g., due to muscle noise), three of the bipolar leads 204 are present from which an ECG signal may be generated without an artifact. In the case of QRS detection, an artifact may be detected and rejected before being output by a cardiograph device, assuming the amount of time to detect the artifact is less than the QRS detector delay. Thus, the QRS detector may exclude bipolar leads determined to contain the artifact, and rely on bipolar leads without the detected artifact present to detect the QRS in the ECG signal. Other ECG analyses, such as arrhythmia analysis, may accept a similarly short delay to receive a signal in order to exclude bipolar leads with an artifact to be excluded from analysis. In some examples, an artifact may be present on all except two electrodes in order to maintain an artifact-free ECG signal on at least one bipolar lead.

Figure 3:
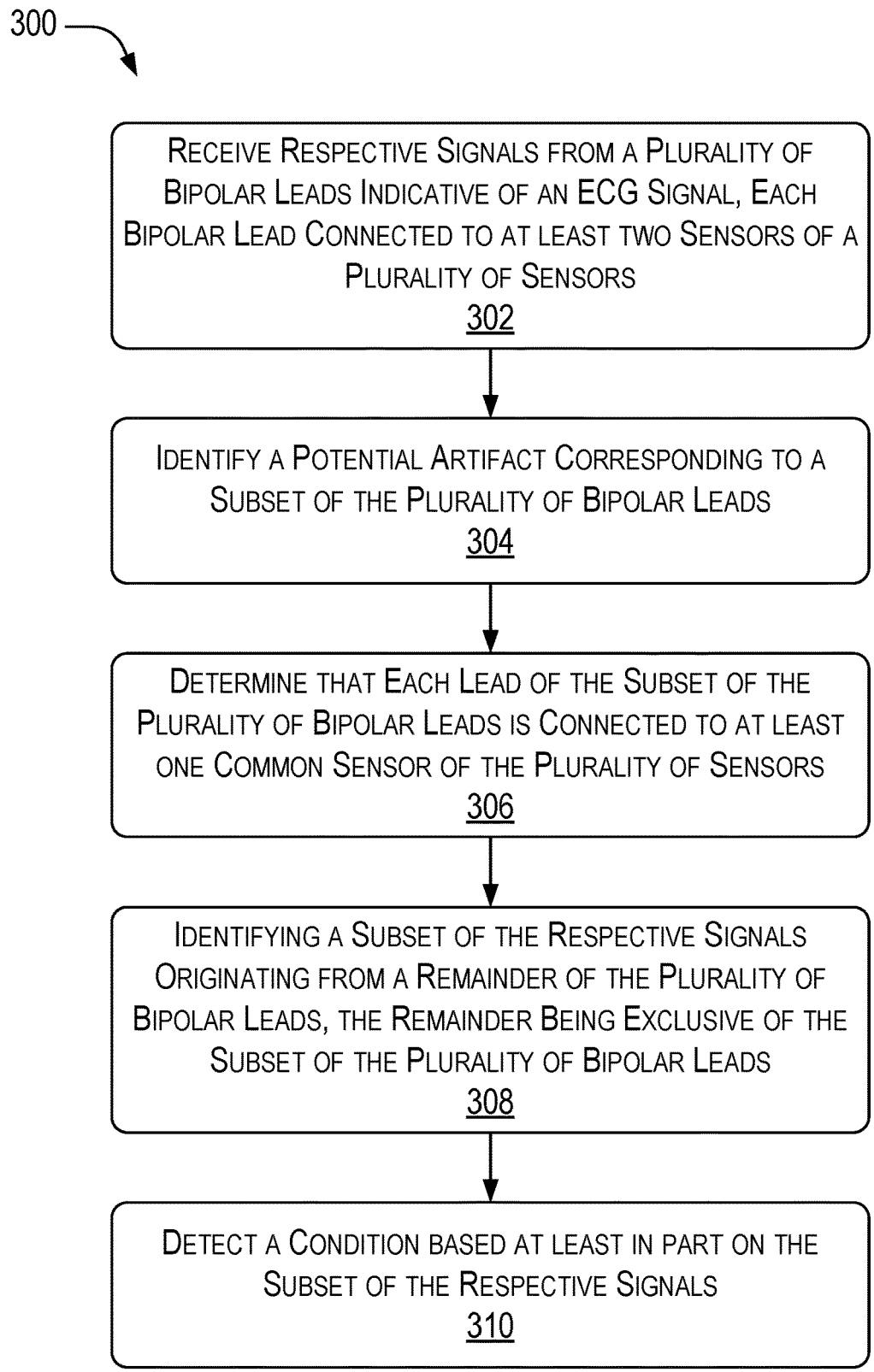
FIG. 3 is an example process for detecting an artifact from a signal according to the techniques described herein.

FIG. 3 provides a flow chart illustrating an example process 300 for detecting an artifact from a signal according to the techniques described herein. In some examples, one or more operations of the process 300 may be combined with one or more operations of the process 400 illustrated in FIG. 4. In some examples, the process 300 may be performed by one or more computing devices, such as the cardiograph device 102 of FIG. 1.

The process can include, at operation 302, receiving, by a cardiograph device, respective signals from a plurality of bipolar leads indicative of an ECG signal, where each bipolar lead of the plurality of bipolar leads is connected to two sensors of a plurality of sensors. In some examples, the plurality of sensors may be electrodes comprising one or more conductive pads attached to the body surface of a patient. The sensors may be positioned on the patient's body in a conventional lead system, a Mason-Likar exercise lead system, or alternative lead system, to sense the patient's cardiac electrical activity. In such examples, at 302, one or more such sensors may direct a respective signal(s) to a processor or other component of the cardiograph device via the bipolar leads, and at 302, the processor or other component of the electrocardiograph device may receive such signals.

At operation 304, the process can include identifying, by the processor of the cardiograph device, a potential artifact corresponding to a subset of a plurality of bipolar leads. In some examples, the cardiograph device may identify the potential artifact by determining differences in the electrical signals output from different ones of the plurality of sensors, as described in more detail in relation to FIGS. 4 and 5. As described above, each bipolar lead may connect between two different sensors to detect the electrical potential difference between the two different sensors. In some examples, all of the bipolar leads may output an artifact, in which case the ECG system may analyze the signals output by all of the bipolar leads (or a subset of the bipolar leads selected by a clinician, as described above).

At operation 306, the process can include determining, by the processor of the cardiograph device, that each lead of the subset of the plurality of bipolar leads is connected to at least one common sensor of the plurality of sensors. For instance, in an ECG system with four electrodes and six bipolar leads, each electrode may be present in three of the bipolar leads. Therefore, if an artifact originates from one of the four sensors due to muscle noise at the location of the sensor, the three bipolar leads connected to the one sensor may display the artifact.

At operation 308, the process can include identifying, by the processor of the cardiograph device, a subset of the respective signals originating from a remainder of the plurality of bipolar leads, the remainder being exclusive of the subset of the plurality of bipolar leads. In other words, the cardiograph device identifies bipolar leads that do not display the artifact. Continuing with the example above at the operation 306, the cardiograph device may identify the three bipolar leads that are not connected to the one sensor where the artifact was detected.

At operation 310, the process can include detecting, by the processor of the cardiograph device, a condition based at least in part on the subset of the respective signals. Examples of conditions may include a QRS complex, an arrhythmia, hypertension, myocardial infarction, medication monitoring, murmurs, and so forth. For instance, the cardiograph device may exclude electrical signals originating from bipolar leads connected to a sensor where an artifact is detected from analysis, where the electrical signals from the remaining bipolar leads are used for QRS detection.

While the description provided herein (including the description of the process 300) generally relates to a cardiograph device having bipolar leads each connected to two sensors, other examples are also considered. For instance, the cardiograph device 102 may reference a Wilson terminal (or central terminal) to average three recorded limbs (right arm, left arm and left leg) which form the Einthoven triangle and are generally electrically equidistant from the electrical center of the heart. The Wilson terminal may generate a signal according to $V=C-(LA+LL+RA)/3$, where V is the potential difference between the precordial electrode and the center of the heart, C is the signal received at the central terminal, LA is the signal received at the left arm sensor, LL is the signal received at the left leg sensor, and RA is the signal received at the right arm sensor. Given Wilson-referenced leads I, II, and $V_x$ as inputs, for example, the patient management system 106 may derive the bipolar leads according to the following:

$$(L - R) = I$$

$$(F - R) = II$$

$$(F - L) = II - I$$

$$(C_x - R) = V_x + \frac{(I + II)}{3}$$

$$(C_x - L) = V_x + \frac{(I + II)}{3 - I}$$

$$(C_x - F) = V_x + \frac{(I + II)}{3 - II}$$

In the derivation above, $V_x$ corresponds to the Wilson-referenced lead and $C_x$ corresponds to the electrode for the Wilson-referenced lead. Accordingly, the patient management system 106 may electronically reference the central terminal, and use the Wilson-referenced leads to derive the bipolar leads to detect an artifact as described herein. Alternatively or additionally, the cardiograph device 102 may generate augmented unipolar limb leads (e.g., aVR, aVL, aVF, etc.), and use the augmented unipolar limb leads to derive three limb leads I, II, and III. Each of the unipolar limb leads comprise a single positive electrode that is referenced against a combination of the other limb electrodes. The cardiograph device 102 may use the three limb leads to derive the bipolar lead signals. Therefore, the bipolar leads may not be directly connected to the sensors, but rather derived from lead signals produced by the cardiograph device 102.

Figure 4:
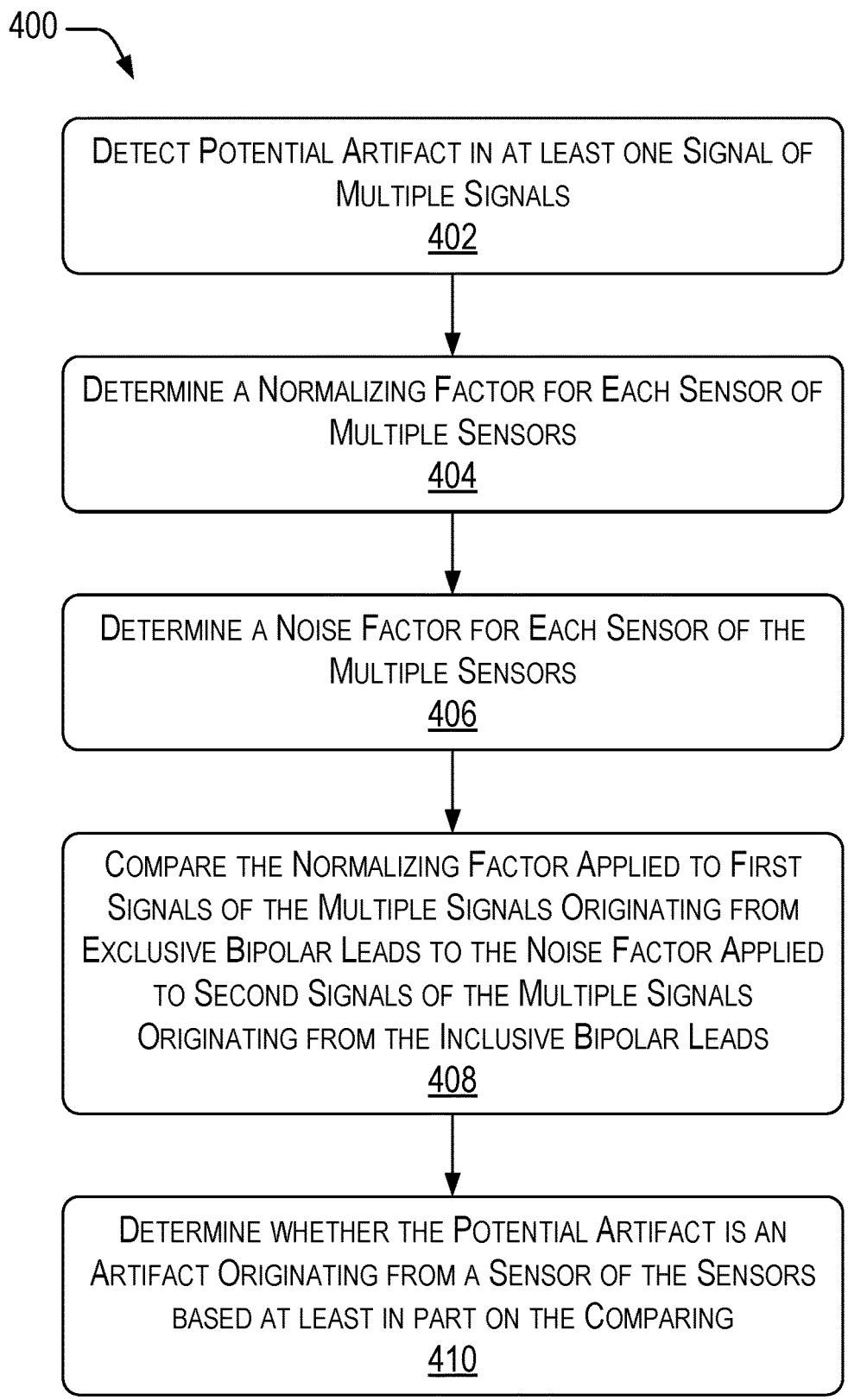
FIG. 4 is an example process for utilizing a noise factor and a normalizing factor applied to signals from an ECG system to detect an artifact in the signals according to the techniques described herein.

FIG. 4 provides a flow chart illustrating an example process 400 for utilizing a noise factor and a normalizing factor applied to signals from an ECG system to detect an artifact in the signals according to the techniques described herein. In some examples, one or more operations of the process 400 may be combined with one or more operations of the process 300 illustrated in FIG. 3. In some examples, the process 400 may be performed by one or more computing devices, such as the cardiograph device 102 of FIG. 1. Reference will be made throughout the discussion of the process 400 to FIG. 5, which shows a diagram of components of an ECG system 500 in which an artifact has been detected in a sensor. Components of the ECG system 500 may correspond to components of the ECG system of FIG. 2.

At operation 402, a cardiograph device detects a potential artifact. For instance, the cardiograph device may detect the potential artifact by applying a high pass filter (or other filter type) to detect signals that deviate from an expected value. In such examples, at 402, a processor or other component of the cardiograph device may receive signals from one or more sensors as described above in relation to operation 302, and the processor or other component of the electrocardiograph device may utilize such to detect the potential artifact. In the ECG system 500, an R sensor 502(1) has been identified as having a potential artifact. In some examples, a square of a 16-millisecond (ms) first difference can be used as a filter, where an expected value of a 16 ms squared difference of L–R corresponds to:

$$<(L-R)^2> = <L^2+R^2-2*RL> \tag{1}$$

Figure 5:
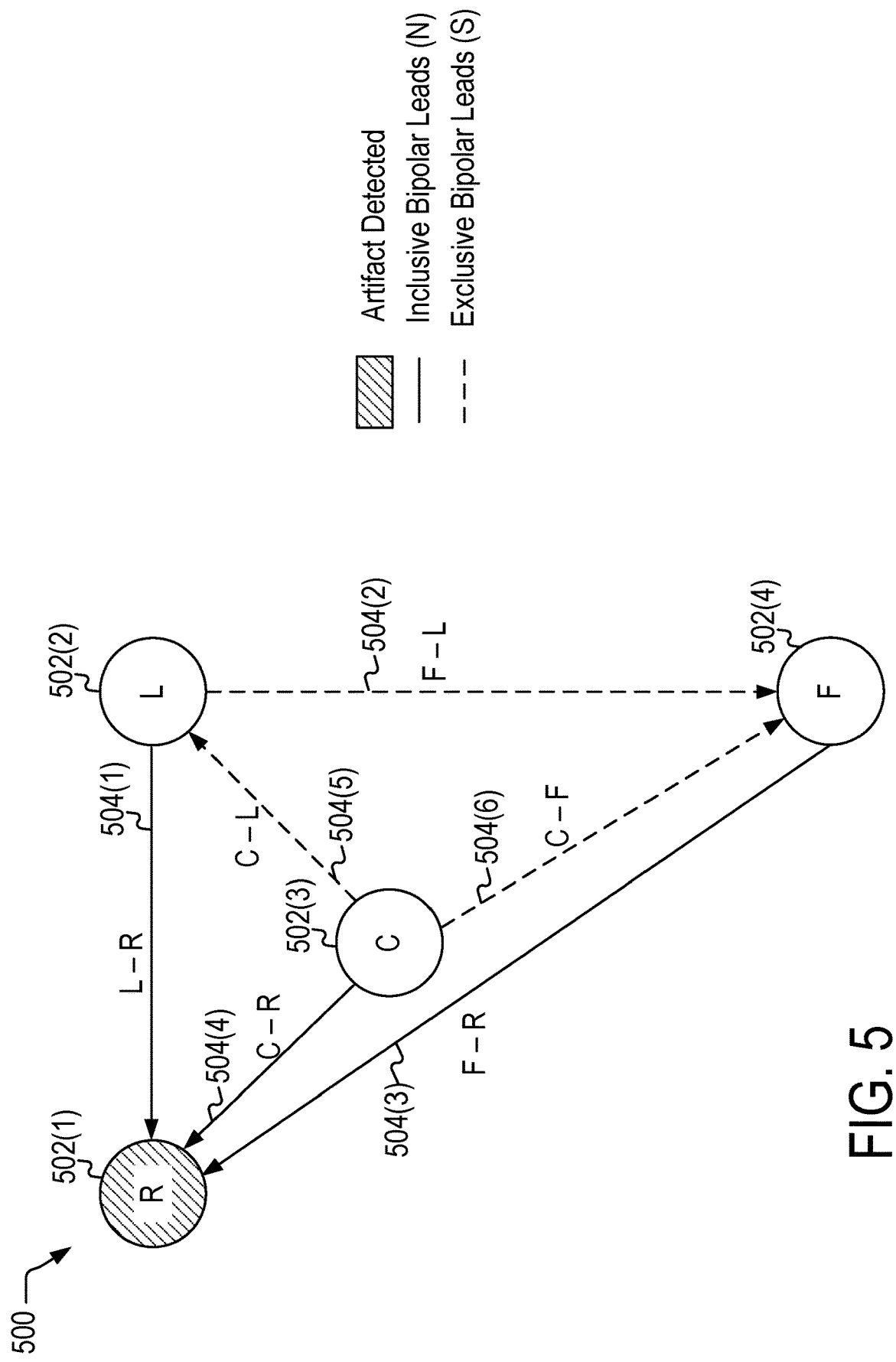
FIG. 5 shows a diagram of components of an ECG system in which an artifact has been detected in a sensor.

In the context of electrode noise as a potential artifact, the R sensor (e.g., the R sensor 502(1) of FIG. 5) and an L sensor (e.g., an L sensor 502(2) of FIG. 5) are typically uncorrelated, as these sensors are attached to different portions of the body. Therefore, an expected value of 2RL is approximately zero (for zero mean R and L). Thus, Equation 1 above can be simplified to:

$$<(L-R)^2> = <L^2+R^2> \tag{2}$$

Three bipolar leads 504(1), 504(3), and 504(4) are connected to the R sensor 502(1), and are denoted by solid lines indicating a group of inclusive bipolar leads N. Thus, the inclusive bipolar leads include the R sensor 502(1) in which a potential artifact has been detected. Three bipolar leads 504(2), 504(5), and 504(6) of the ECG system 500 do not involve the R sensor 502(1), and are denoted by dashed lines indicating a group of exclusive bipolar leads S. Thus, the exclusive bipolar leads do not include the R sensor 502(1) in which the potential artifact has been detected. Expected values of the inclusive bipolar leads N and expected values of the exclusive bipolar leads S may be combined (e.g., summed, multiplied, according to a weighted summation, etc.), such as according to the following:

$$N = <(L-R)^2> + <(F-R)^2> + <(C-R)^2> = 3*(<R^2> + <L^2> + <F^2> + <C^2>) \tag{3}$$

$$S = <(F-L)^2> + <(C-L)^2> + <(C-F)^2> = 2*(<L^2> + <F^2> + <C^2>) \tag{4}$$

The term N has contribution from R, while the term S does not. Thus, a relative comparison between N and S can be used to determine if there is noise in R. Similar comparisons can be made for any number of sensors (e.g., any of the sensors 502, or others) to determine whether noise is present in an individual sensor.

In some examples, the expected value sum of S is taken over a 160 ms time period, and the expected value sum of N is taken over a 80 ms time period, where the time period for the inclusive bipolar leads N is centered on the time period for the exclusive bipolar leads S, although other example time periods are also considered. Utilizing these time periods yields an approximately 80 ms artifact detection delay. A shorter time period utilized for N than for S may be used to account for depolarization beginning earlier in some bipolar leads than others, and it may be undesirable for slight differences in initiation of depolarization to contribute to artifact detection. As just noted, other time periods may be used to emphasize artifacts of different durations, and/or to reduce or increase the artifact detection delay.

Returning to the process 400, an operation 404 includes determining, by the processor of the cardiograph device, a normalizing factor for each sensor of multiple sensors. The normalizing factor is used to scale the signal strength based on a long-term measure of the average or typical power of the artifact-free signal; use of the normalizing factor is described in detail below. The normalizing factor, referred to herein as "P," may be determined by the cardiograph device for each of the sensors 502 of the ECG system 500 over a fixed time period (e.g., 9 seconds, 10 seconds, etc.), or other time periods to detect specific artifacts. In one example, the cardiograph device may trigger the normalizing factor P to update based on detecting a QRS complex that has a morphological match to a previously detected QRS complex. When this trigger occurs, the cardiograph device may compute a sum of squared 16 ms differences (referred to herein as "Sp"), over a time period centered on the detected QRS complex for all of the bipolar leads. In some examples, the cardiograph device may compute Sp over a time period of 160 ms, although other time periods are also considered. The cardiograph device may, in some cases, filter Sp with a low-pass infinite impulse response (IIR) filter with a time constant (e.g., 9 seconds) to compute Spf for each bipolar lead, using the following:

$$Spf(n) = \left(1 - \frac{1}{64}\right) * Spf(n-1) + \frac{1}{64} * Sp \tag{5}$$

Where n is the trigger count.

In another example, the cardiograph device may calculate Spf by filtering S (e.g., the electrical signals from the exclusive bipolar leads) with a longer time constant (e.g., 9 seconds) low-pass IIR filter every sample. In this case, a QRS detection time is not required to trigger an update to Spf. Of course, other types of filters may be used in either example to compute Spf.

The cardiograph device may compute the normalizing factor, P, for each sensor as a ratio of the sum of Spf terms with a particular sensor (e.g., the inclusive bipolar leads N) to the sum of the Spf terms without the particular sensor (e.g., the exclusive bipolar leads S). For example, the cardiograph device may compute the normalizing factor P for the R sensor 502(1) of FIG. 5 as:

$$P(R) = \frac{Spf(L-R) + Spf(F-R) + Spf(C-R)}{Spf(F-L) + Spf(C-L) + Spf(C-F)} \tag{6}$$

The cardiograph device may compute P similarly for each of the sensors 502.

Again returning to FIG. 4, an operation 406 includes the processor of the cardiograph device determining a noise factor (referred to herein as "Nf") for each sensor of the multiple sensors. The cardiograph device may use the noise factor to reduce the likelihood of detecting, as an artifact, a beat such as a premature ventricular contraction (PVC) that has most of the power of the signal in a direction of a single electrode sensor. In some examples, the cardiograph device may determine the noise factor by first computing a single, 16 ms sample first difference of a current electrical signal minus a previous single sample (dS1) and a 16 ms first difference of the previous single sample minus a second-previous single sample (dS2). For all bipolar leads that share an electrode (e.g., inclusive bipolar leads N), if the signs of dS1 and dS2 do not match, and an absolute value of dS1 and an absolute value of dS2 are greater than a threshold amount (e.g., 0.025 mV), the cardiograph device may assign a value to the signal from the bipolar leads (e.g., p=1). On the other hand, if the signs of dS1 and dS2 do match, and/or an absolute value of dS1 and an absolute value of dS2 are less than the threshold amount (e.g., 0.025 mV), the cardiograph device may assign a different value to the signal from the bipolar leads (e.g., p=0). The noise factor term, Nf, is the sum of p over a time period (e.g., 160 ms), divided by a number of samples over the time period.

In examples, Nf may be equal to 1 when each sample contains a peak such as when the waveform of the signal is changing directions every sample. On the other hand, Nf may be equal to 0 for a flat (e.g., low noise) or monotonically increasing or decreasing signal. Of course, other filters may be used to emphasize different frequencies, bands of frequencies, or morphological characteristics than those discussed herein when calculating a noise factor Nf.

An operation 408 includes the processor of the cardiograph device comparing the normalizing factor applied to first signals of the multiple signals originating from exclusive bipolar leads to the noise factor applied to second signals of the multiple signals originating from the inclusive bipolar leads. For instance, a comparison between the normalizing factor P applied to signals originating from exclusive bipolar leads to the noise factor Nf applied to signals originating from the inclusive bipolar leads may be based on the following:

$$N(elec)*Nf(elec) \leftrightarrow S(elec)*P(elec) \tag{7}$$

Where elec corresponds to a particular electrode sensor (e.g. any sensor from sensors 202). To determine N(elec) and P(elec), the cardiograph device may first determine a sum of squared 16 ms differences for each of the bipolar leads 504 over the time period for N (e.g., 80 ms) and computed over the time period for S (e.g., 160 ms). Ratios for each bipolar lead, rN and rS, may be computed as:

$$rN(lead) = \frac{N(lead)}{Spf(lead) + 0.025 \text{ mV}} \tag{8}$$

$$rS(lead) = \frac{S(lead)}{Spf(lead) + 0.025 \text{ mV}} \tag{9}$$

The cardiograph device may apply an offset of 0.025 mV in the denominators of the Equations (8) and (9), which may reduce the ratio for quiescent signals. Other values for the offset are also considered.

For each electrode, the N term may be the sum of the per-lead rN term as determined in Equations (8), and the S term may be the sum of the per-lead rS term as determined in Equation (9), such as based on the following:

$$N(elec) = sum(rN(leads), set_{with}) \tag{10}$$

$$S(elec) = Sum(rS(leads), set_{without}) \tag{11}$$

An operation 410 includes the processor of the cardiograph device determining whether the potential artifact is an artifact originating from a sensor of the sensors based at least in part on the comparing. For instance, if the inclusive set of leads N has a greater signal value with the noise factor applied than the signal produced by the exclusive set of leads with the normalizing factor applied, then the cardiograph device may determine that the potential artifact is likely an artifact associated with electrical activity of muscle close to the sensor rather than cardiac electrical activity. A determination of an artifact may be based on Equation (7), modified as follows:

$$N(elec)*Nf(elec) > S(elec)*P(elec) \tag{12}$$

As noted above, combinations of N and S terms that select multiple or different bands of frequencies or morphological characteristics than those described herein may also be used to detect artifacts.

Figure 6:
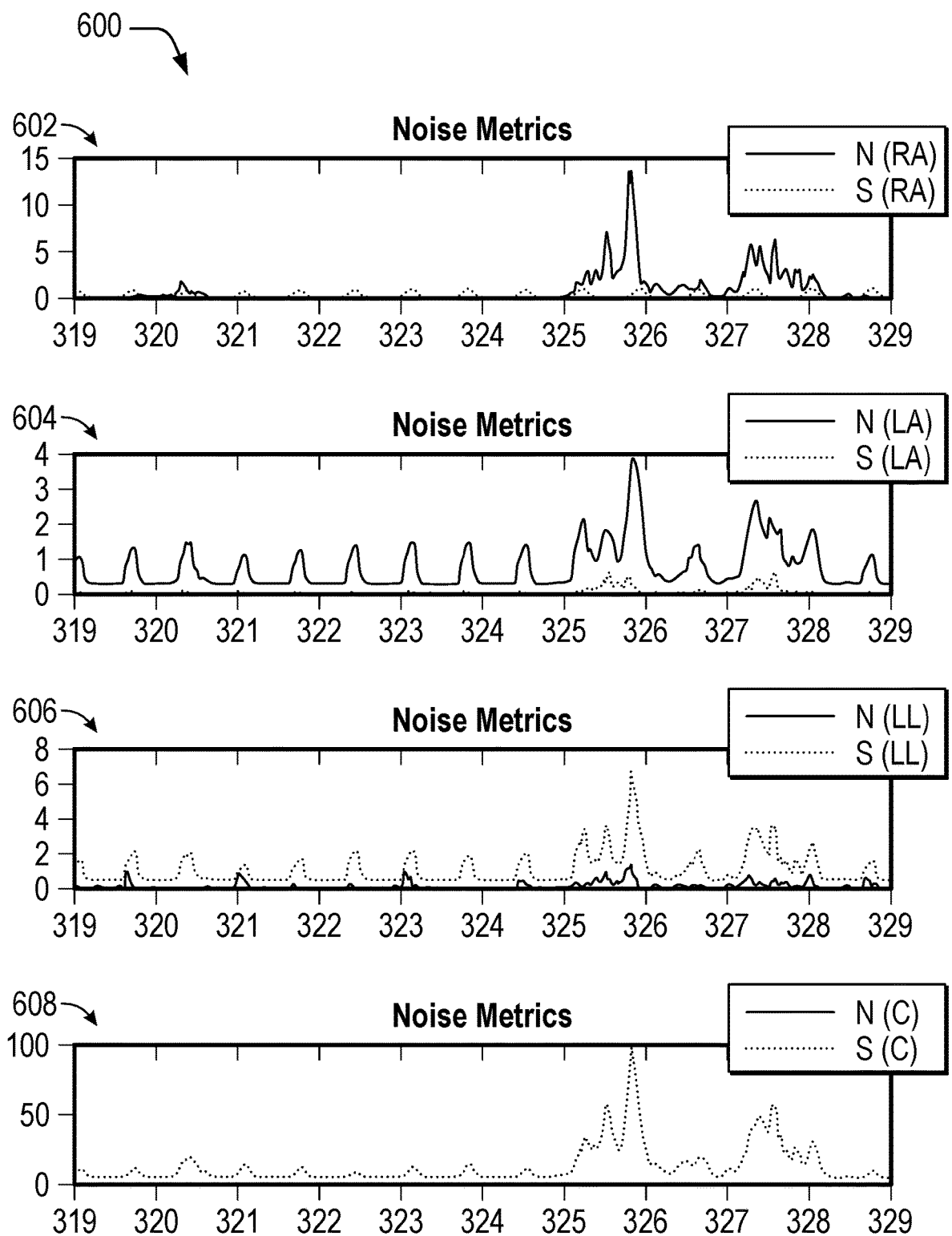
FIG. 6 illustrates example outputs of an ECG system based on inclusive and exclusive bipolar leads that include an artifact detected using the described techniques.

FIG. 6 illustrates example outputs 600 of an ECG system based on inclusive and exclusive bipolar leads that include an artifact detected using the described techniques. The example outputs 600 display electrical signal magnitude versus time (seconds). A first graph 602 depicts signal values of N (inclusive bipolar leads) and signal values of S (exclusive bipolar leads) relative to the right arm (RA) sensor of an ECG system. A second graph 604 depicts signal values of N and signal values of S relative to the left arm (LA) sensor of the ECG system. A third graph 606 depicts signal values of N and signal values of S relative to the left leg (LL) sensor of the ECG system. A fourth graph 608 depicts signal values of N and signal values of S relative to the precordial (C) sensor(s) of the ECG system. In this example, a noise artifact is detected whenever N*Nf>S*P, which occurs when the line representing N crosses the line representing S. In the depicted example outputs 600, this occurs on the first graph 602 around 320 seconds, and again around 325 seconds.

Figure 7:
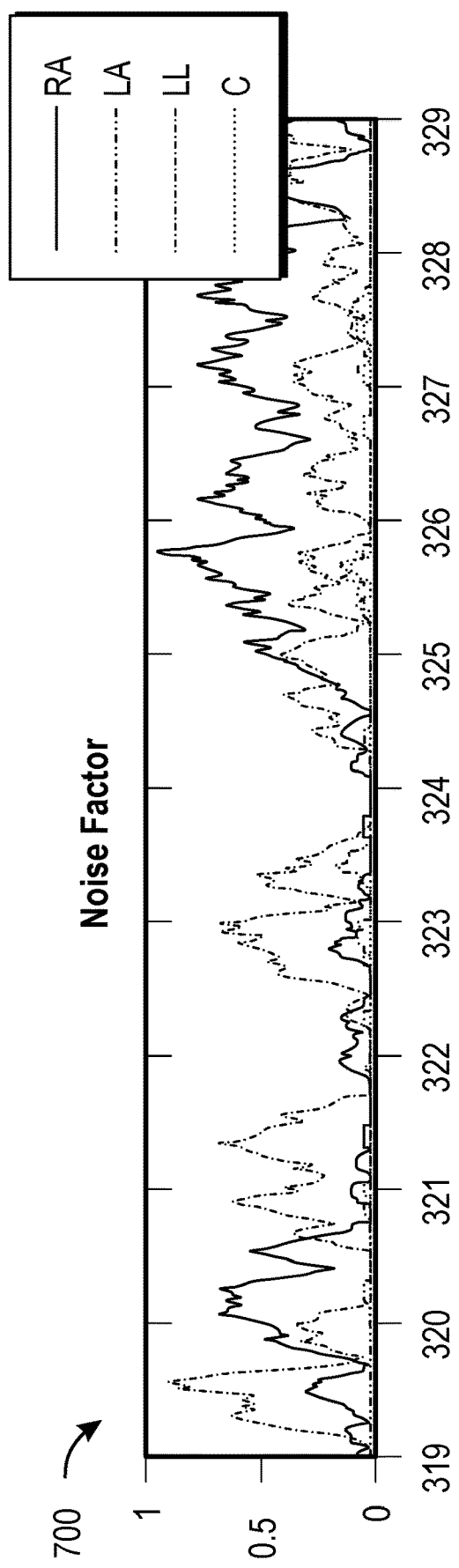
FIG. 7 illustrates an example output of an ECG system based on noise factors for different sensors detected using the described techniques.

FIG. 7 illustrates an example output 700 of an ECG system based on noise factors for different sensors detected using the described techniques. The example output 700 displays the noise factor Nf calculated as described above versus time (seconds), and corresponds to a similar time period as the example outputs 600 of FIG. 6. The example output 700 includes noise factors calculated for each of the right arm (RA) sensor, the left arm (LA) sensor, the left leg (LL) sensor, and the precordial (C) sensor(s) of the ECG system. While the noise factors calculated for the RA sensor and the LL sensor are both relatively high compared to the LA and C sensors, this may be due to a large number of peaks on bipolar leads containing RA and leads containing LL, even though the amplitudes of peaks on some leads with LL (e.g., C-LL) are small. However, the N term as described in relation to FIG. 6 is high only for RA, so the noise artifact is only detected on this particular sensor.

The example systems and methods of the present disclosure overcome various deficiencies of known prior art devices. Other embodiments of the present disclosure will be apparent to those skilled in the art from consideration of the specification and practice of the disclosure contained herein. It is intended that the specification and examples be considered as example only, with a true scope and spirit of the present disclosure being indicated by the following claims.

What is claimed is:

1. A system comprising:
    a processor;
    a plurality of sensors in communication with the processor and configured to sense an electrocardiograph (ECG) signal;
    a plurality of bipolar leads connected to the plurality of sensors, such that a bipolar lead of the plurality of bipolar leads connects to two sensors of the plurality of sensors to determine an electrical potential difference between the two sensors; and
    computer-readable media storing instructions that, when executed by the processor, cause the processor to perform operations comprising:
        receiving, substantially continuously, respective signals from the plurality of bipolar leads indicative of the ECG signal;
        identifying, based on the respective signals and substantially in real time as the respective signals are received, a potential artifact corresponding to a subset of the plurality of bipolar leads;
        determining that each lead of the subset of the plurality of bipolar leads is connected to at least one common sensor of the plurality of sensors;
        based on the determining, identifying a subset of the respective signals originating from a remainder of the plurality of bipolar leads, wherein the remainder is exclusive of the subset of the plurality of bipolar leads; and
        detecting a condition of a patient based at least in part on the subset of the respective signals.

2. The system of claim 1, wherein the plurality of sensors comprises at least three individual electrode sensors and the plurality of bipolar leads comprises at least three individual bipolar leads, and wherein each individual bipolar lead is connected to two different sensors of the at least three individual electrode sensors.

3. The system of claim 2, wherein the ECG signal comprises a first ECG signal and the system further comprises a display device in communication with the processor, the operations further comprising:
    generating a second ECG signal based on the subset of the respective signals and exclusive of signals received from the remainder of the plurality of bipolar leads; and
    causing the display device to provide an output indicative of the second ECG signal.

4. The system of claim 1, wherein:
    identifying the potential artifact comprises determining expected values corresponding to each of the respective signals by applying a filter to each of the respective signals, and
    identifying the potential artifact substantially in real time results in an artifact detection delay of less than one second.

5. The system of claim 4, wherein identifying the potential artifact further comprises:
    determining a difference between:
        a first subset of the expected values corresponding to the subset of the plurality of bipolar leads, and
        a second subset of the expected values corresponding to the remainder of the plurality of bipolar leads; and
    determining that noise is present in the subset of the plurality of bipolar leads based at least in part on the difference.

6. The system of claim 5, wherein the first subset of the expected values is determined within a first time period and the second subset of the expected values is determined within a second time period, the first time period and the second time period having different durations.

7. The system of claim 1, wherein the condition is a first QRS complex, the operations further comprising:
    detecting a second QRS complex, the second QRS complex occurring before the first QRS complex;
    determining a first time period during which the first QRS complex occurred;
    determining a second time period during which the second QRS complex occurred;
    determining a difference between a first signal value included in the first time period and a second signal value included in the second time period;
    generating values corresponding to each bipolar lead by applying a low-pass filter to the difference; and
    determining a normalizing factor for a particular sensor of the plurality of sensors based at least in part on the values.

8. The system of claim 7, wherein the operations further comprise:
    determining a first sum of a first subset of the values corresponding to the particular sensor of the plurality of sensors;
    determining a second sum of a second subset of the values corresponding to remaining values of the values; and
    determining the normalizing factor for the particular sensor based at least in part on a ratio of the first sum to the second sum.

9. The system of claim 1, wherein the operations further comprise:
    determining, for a particular signal of the respective signals corresponding to a particular sensor of the plurality of sensors, a first difference between the particular signal and a first prior signal generated by the particular sensor and associated with a first time;

determining a second difference between the particular signal and a second prior signal generated by the particular sensor and associated with a second time; and determining a noise factor for the particular sensor based at least in part on:
 determining that one of the first difference and the second difference is a negative value;
 determining that a different one of the first difference and the second difference is a positive value;
 determining that a first absolute value of the first difference is greater than a threshold amount; and
 determining that a second absolute value of the second difference is greater than the threshold amount.

10. The system of claim 9, wherein the first time and the second time correspond to a same time sample within a first period and a second period, respectively, and wherein determining the noise factor further comprises:
 assigning a first value to the particular signal responsive to determining the negative value and the positive value;
 determining that the first absolute value and the second absolute value are greater than the threshold amount; and
 determining a sum of the first value with one or more other values determined for the first period to determine the noise factor.

11. The system of claim 1, wherein the operations further comprise detecting an artifact of the patient based at least in part on comparing a noise factor applied to signals originating from the subset of the plurality of bipolar leads with a normalizing factor applied to the subset of the respective signals originating from the remainder of the plurality of bipolar leads.

12. A method comprising:
 receiving, substantially continuously, respective signals from a plurality of bipolar leads indicative of an electrocardiograph (ECG) signal, each bipolar lead of the plurality of bipolar leads connected to two sensors of a plurality of sensors;
 identifying, based on the respective signals and substantially in real time as the respective signals are received, a potential artifact corresponding to a subset of the plurality of bipolar leads;
 determining that each lead of the subset of the plurality of bipolar leads is connected to at least one common sensor of the plurality of sensors;
 based on the determining, identifying a subset of the respective signals originating from a remainder of the plurality of bipolar leads, wherein the remainder is exclusive of the subset of the plurality of bipolar leads; and
 detecting a condition of a patient based at least in part on the subset of the respective signals.

13. The method of claim 12, wherein the condition is a first QRS complex, the method further comprising:
 detecting a second QRS complex, the second QRS complex occurring before the first QRS complex;
 determining a first time period during which the first QRS complex occurred;
 determining a second time period during which the second QRS complex occurred;
 determining a difference between a first signal value included in the first time period and a second signal value included in the second time period;
 generating values corresponding to each bipolar lead by applying a low-pass filter to the difference; and
 determining a normalizing factor for a particular sensor of the plurality of sensors based at least in part on the values.

14. The method of claim 13, further comprising:
 determining a first sum of a first subset of the values corresponding to the particular sensor of the plurality of sensors;
 determining a second sum of a second subset of the values corresponding to remaining values of the values; and
 determining the normalizing factor for the particular sensor based at least in part on a ratio of the first sum to the second sum.

15. The method of claim 12, further comprising:
 determining, for a particular signal of the respective signals corresponding to a particular sensor of the plurality of sensors, a first difference between the particular signal and a first prior signal generated by the particular sensor and associated with a first time;
 determining a second difference between the particular signal and a second prior signal generated by the particular sensor and associated with a second time; and
 determining a noise factor for the particular sensor based at least in part on:
  determining that one of the first difference and the second difference is a negative value;
  determining that a different one of the first difference and the second difference is a positive value;
  determining that a first absolute value of the first difference is greater than a threshold amount; and
  determining that a second absolute value of the second difference is greater than the threshold amount.

16. The method of claim 15, wherein the first time and the second time correspond to a same time sample within a first period and a second period, respectively, and wherein determining the noise factor further comprises:
 assigning a first value to the particular signal responsive to determining the negative value and the positive value;
 determining that the first absolute value and the second absolute value are greater than the threshold amount; and
 determining a sum of the first value with one or more other values determined for the first time period to determine the noise factor.

17. One or more computer-readable media storing instructions, which when executed by one or more processors, cause the one or more processors to perform operations comprising:
 receiving, substantially continuously, respective signals from a plurality of bipolar leads indicative of an electrocardiograph (ECG) signal, each bipolar lead of the plurality of bipolar leads connected to two sensors of a plurality of sensors;
 identifying, based on the respective signals and substantially in real time as the respective signals are received, a potential artifact corresponding to a subset of the plurality of bipolar leads;
 determining that each lead of the subset of the plurality of bipolar leads is connected to at least one common sensor of the plurality of sensors;
 based on the determining, identifying a subset of the respective signals originating from a remainder of the plurality of bipolar leads, wherein the remainder is exclusive of the subset of the plurality of bipolar leads; and detecting a condition of a patient based at least in part on the subset of the respective signals.

18. The one or more computer-readable media of claim 17, wherein identifying the potential artifact comprises determining expected values corresponding to each of the respective signals by applying a high-pass filter to each of the respective signals.

19. The one or more computer-readable media of claim 18, wherein identifying the potential artifact further comprises:

determining a difference between:
   a first subset of the expected values corresponding to the subset of the plurality of bipolar leads, and
   a second subset of the expected values corresponding to the remainder of the plurality of bipolar leads; and
determining that noise is present in the subset of the plurality of bipolar leads based at least in part on the difference.

20. The one or more computer-readable media of claim 17, wherein the operations further comprise detecting an artifact of the patient based at least in part on comparing a noise factor applied to signals originating from the subset of the plurality of bipolar leads with a normalizing factor applied to the subset of the respective signals originating from a remainder of the plurality of bipolar leads.

* * * * *